United States Patent
Yu et al.

(10) Patent No.: US 8,911,597 B2
(45) Date of Patent: Dec. 16, 2014

(54) METHOD OF PREPARING DOUBLE-LAYER ANTIMICROBIAL COATING

(75) Inventors: Shui Yu, Xiamen (CN); Zi-bao Wu, Xiamen (CN); Hai-xia Zhou, Xiamen (CN); Min-Zen Lee, Xiamen (CN)

(73) Assignee: Xiamen Runner Industrial Corporation, Xiamen (CN)

( * ) Notice: Subject to any disclaimer, the term of this patent is extended or adjusted under 35 U.S.C. 154(b) by 227 days.

(21) Appl. No.: 13/187,734

(22) Filed: Jul. 21, 2011

(65) Prior Publication Data

US 2012/0181177 A1  Jul. 19, 2012

(30) Foreign Application Priority Data

Jan. 18, 2011 (CN) .......................... 2011 1 0021129

(51) Int. Cl.
*C23C 14/34* (2006.01)
*C25D 13/10* (2006.01)
*A01N 59/16* (2006.01)
*C23C 14/20* (2006.01)

(52) U.S. Cl.
CPC .............. *A01N 59/16* (2013.01); *C23C 14/205* (2013.01)
USPC ..................................... 204/192.15; 204/486

(58) Field of Classification Search
USPC .................................................. 204/192.15
See application file for complete search history.

(56) References Cited

U.S. PATENT DOCUMENTS

| | | | | |
|---|---|---|---|---|
| 4,886,681 A | * | 12/1989 | Clabes et al. ................. | 427/525 |
| 4,888,244 A | * | 12/1989 | Masubuchi et al. ........... | 428/416 |
| 5,180,585 A | * | 1/1993 | Jacobson et al. .............. | 424/405 |
| 6,069,142 A | * | 5/2000 | Gaffney et al. ............... | 514/241 |
| 6,367,146 B1 | * | 4/2002 | Han et al. .................... | 29/603.15 |
| 6,594,134 B2 | * | 7/2003 | Yializis ........................ | 361/305 |
| 6,740,393 B1 | * | 5/2004 | Massler et al. ............... | 428/216 |
| 2003/0052000 A1 | * | 3/2003 | Segal et al. ............. | 204/298.13 |
| 2005/0249791 A1 | * | 11/2005 | Hobbs et al. .................. | 424/443 |
| 2006/0008539 A1 | * | 1/2006 | Tomioka ....................... | 424/725 |
| 2006/0198903 A1 | * | 9/2006 | Storey et al. ................. | 424/618 |
| 2007/0035053 A1 | * | 2/2007 | Schulz et al. .................. | 264/2.5 |
| 2008/0050535 A1 | * | 2/2008 | Schmidt et al. ............... | 427/514 |
| 2009/0035952 A1 | * | 2/2009 | Chua et al. .................... | 438/788 |
| 2009/0068089 A1 | * | 3/2009 | Hussain et al. ............... | 423/604 |

* cited by examiner

*Primary Examiner* — Keith Hendricks
*Assistant Examiner* — Stefanie S Wittenberg
(74) *Attorney, Agent, or Firm* — Chun-Ming Shih

(57) ABSTRACT

A method of a preparing double-layer antimicrobial coating comprises: placing a plastic substrate into a PVD vacuum equipment for a vacuum process; rinsing and activating the substrate when the vacuum level reaches $10^{-2}$; coating a metal film onto the activated substrate by the vacuum process; spraying an antimicrobial intermediate coating onto the metal film; and then coating an antimicrobial metal film by PVD to obtain a double-layer antimicrobial layer. The coating has two antimicrobial layers, and includes bores because the density of the coated film layer produced by PVD is low, so that the antimicrobial agent of the antimicrobial intermediate coating can pass through the bores and move to the surface of the coating and the surface of the antimicrobial coating, so as to kill the bacteria or suppress their grown. The method is very suitable for the sanitary, electronics, electrical appliances and the automobile industry.

8 Claims, 1 Drawing Sheet

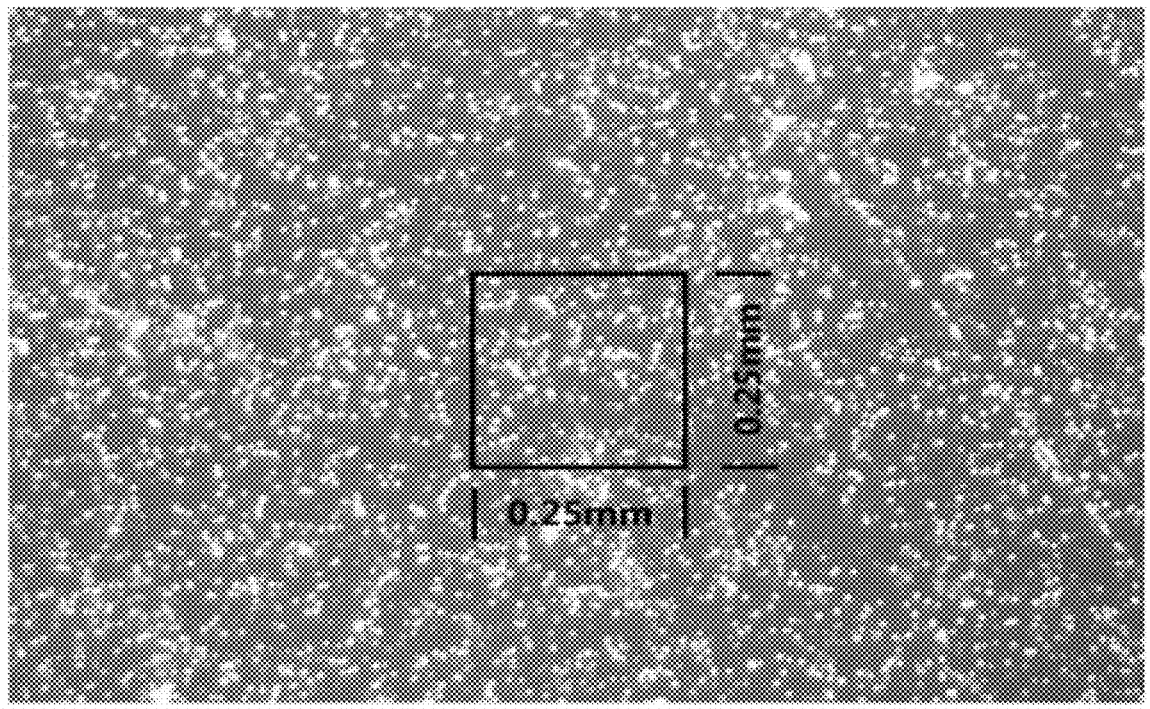

METHOD OF PREPARING DOUBLE-LAYER ANTIMICROBIAL COATING

BACKGROUND OF THE INVENTION

1. Field of the Invention

The present invention generally relates to plastic product metallization, in particular to a novel method of preparing a double-layer antimicrobial coating.

2. Description of Related Art

Since the beginning of the 21$^{st}$ century, plastic products have become an indispensable part of our daily lives as many objects of daily use are made of some kind of plastic. For example, plastic products are used extensively in various electrical appliances (such as telephones, washing machines, computers, and electric switches). With environmental pollution, the plastic products of daily use carry a large quantity of bacteria on the surface of the plastic products and have become a bacterial pollution source or an infection source. Statistics show that approximately 17 million people die each year due to infectious diseases. Therefore, the research and development of novel coating products with the antimicrobial function is significantly important to the issues of improving our living environment, reducing the incidence of diseases, and protecting our health.

Since the global spread of SARS virus in 2003 to the most recent outbreak of H1N1 influenza worldwide, consumers have more concerns about food safety and various pathogens existing in our environment. Antimicrobial agents are used more extensively in the application of plastics than ever to meet the requirements of public health and daily living, and the annual growth rate of antimicrobial agents used in plastics is approximately equal to 3.5%~4%. North America is the world's top user of antimicrobial agents (including biological inhibitors) and consumes approximately 40% of the world total, while Japan consumes 20% of the world total. Japanese has the largest consumption of antimicrobial agents per capita, much greater than North Americans and Europeans. According to a recent survey by the world-renowned public opinion research company Gallup poll, a vast majority of consumers said they are willing to buy antimicrobial products and 75% of the consumers have a preference for antimicrobial products. In the survey, over 7 out of 10 persons revealed that they have used more than six types of antimicrobial products. Consumers generally believe that it is necessary to use the antimicrobial products for different applications and environments.

As disclosed in P.R.C. Pat. No. ZL200420071581, a substrate of an antimicrobial product with an abrasion resistant surface is made of metal, inorganic, or polymer materials, and the surface of such product is coated with a silver, copper, or silver-copper complex film by physical vapor deposition (PVD). However, the coating of the product produced in accordance with this patented technology still has the drawbacks of insufficient abrasion resistance and low sustainability effect.

SUMMARY OF THE INVENTION

Therefore, it is a primary objective of the present invention to overcome the drawbacks of the prior art by providing a method of preparing a double-layer antimicrobial coating with a long-term antimicrobial effect.

The method of preparing a double-layer antimicrobial coating in accordance with the present invention comprises the following steps:

(1) A plastic substrate is placed into a PVD vacuum equipment and processed by a vacuum process. When the vacuum level reaches $10^{-2}$, the substrate is rinsed and activated to obtain an activated substrate.

In Step (1), the plastic substrate is made of thermoplastic or thermosetting plastic, and the thermoplastic is one selected from the group of ABS, PC/ABS, HIPS, PC, PPO, PP, PERT, HDPE, PA6, PA66, ABS/TPU, fiberglass reinforced PA6, and fiberglass reinforced PP, and the thermosetting plastic is BMC The plastic substrate is activated by a plasma glow activation with the following processing conditions: the required current of the ion source falls within a range of 0.3~0.5 A, the bias voltage falls within a range of 80~150V, the duty ratio falls within a range of 50%~80%, the flow of argon falls within a range of 10~100 SCCM, the flow of oxygen falls within a range of 10~150 SCCM, the vacuum pressure in the furnace falls within a range of 0.1~0.3 Pa, and the activation time falls within a range of 5~10 minutes, so as to achieve the effect of cleaning and activating the surface of the substrate and enhancing the adhesion between an antimicrobial dechlorination film and the substrate.

(2) A metal film is coated on a surface of the activated substrate.

In step (2), the metal film is coated on the surface of the substrate by mid-frequency sputtering with the following processing conditions: the mid-frequency power falls within a range of 6~9 kW, the bias voltage falls within a range of 80~150V, the flow of argon falls within a range of 20~100 SCCM, the vacuum pressure in the furnace falls within a range of 0.1~0.3 Pa, the coating time falls within a range of 10~20 minutes, and the metal film is made of at least one selected from the group of Cu, Cr, and Cu—Zn alloy.

(3) The substrate coated with the metal film is sprayed with an antimicrobial intermediate coating.

In step (3), the antimicrobial intermediate coating is made of at least one selected from the group of UV-curing paint, baking paint, electrophoretic paint, and electrostatic powder paint added with an organic antimicrobial agent or an inorganic antimicrobial agent; the UV-curing paint is an UV paint; the organic antimicrobial agent is at least one selected from the group of dichlorooctylisothiazolinone (DCOIT), 3-(trimethoxysilyl)propyldimethyloctadecylammonium (DC5700), 10,10'oxybis-phenoxarsine (OBPA), phosphate complex, PolySept L type antimicrobial agent; the dichlorooctylisothiazolinone (DCOIT) is a vinyzene produced by Rohm and Haas Company; the 3-(trimethoxysilyl)propyldimethyloctadecylammonium is produced by Dow Corning Corporation; the 10,10'oxybis-phenoxarsine (OBPA) is produced by Troy Corporation; the phosphate complex is produced by PolyChem Alloy Inc.; and the inorganic antimicrobial agent is at least one selected from the group of nano silver and nano copper. In addition, the substrate coated with the metal film is sprayed with an antimicrobial intermediate coating by a method as described below:

A plastic substrate is coated with a layer of paint added with 1%~10% of antimicrobial agent, and then sent into an infrared oven for leveling and baking the painted coating, and the dry plastic substrate with the coated paint layer is placed into an ultraviolet curing furnace and processed by a radiation curing crosslink, wherein the radiation curing crosslink time falls within a range of 10~45 seconds; the paint layer has a thickness falling within a range of 10~30 μm; the baking temperature falls within a range of 50~70° C., the baking time falls within a range of 3~10 minutes; the paint layer is an UV paint layer, an electrophoretic paint layer or a powder paint layer.

(4) The sample of the antimicrobial intermediate coating is coated with an antimicrobial metal film by PVD to obtain a double-layer antimicrobial layer.

In step (4), an arc plating method or a mid-frequency sputtering method is adopted for coating the antimicrobial metal film by PVD, wherein the arc plating method is carried out with the following processing conditions: the required current source falls within a range of 60~100 A; the bias voltage falls within a range of 80~150V; the flow of argon falls within a range of 20~100 SCCM; the vacuum pressure in the furnace falls within a range of 0.1~0.3 Pa; and the coating time falls within a range of 1~5 minutes. The mid-frequency sputtering method is carried out with the following processing conditions: The mid-frequency power falls within a range of 6~9 kW; the bias voltage falls within a range of 80~150V; the flow of argon falls within a range of 20~100 SCCM; the vacuum pressure in the furnace falls within a range of 0.1~0.3 Pa; the coating time falls within a range of 5~10 minutes; the target material of the antimicrobial metal film is an alloy target material with 95%~99.5% of Cr and 5%~0.5% of Ag.

Compared with the prior art, the present invention has the following outstanding advantages:

(1) The coating has two antimicrobial layers, and includes a large number of bores because the density of the coated film layer produced by PVD is low, such that the antimicrobial agent of the antimicrobial intermediate coating can pass through the bores and move to the surface of the coating and the surface of the antimicrobial coating, so as to kill the bacteria or suppress their growth.

(2) The coating includes a large number of bores since the density of the coated film layer produced by PVD is low, such that the antimicrobial agent of the antimicrobial intermediate coating can pass through the bores and move to the surface of the coating and the surface of the antimicrobial coating. Therefore, the double-layer antimicrobial layer not only provides the long-term antimicrobial effect, but also achieves a high bacteria suppression rate.

(3) The double-layer metal film/antimicrobial layer/metal antimicrobial film technology has opened up the field of plastic metallization and related products with excellent function and good appearance are very suitable for the sanitary, electronics, electric appliance and automobile industries.

BRIEF DESCRIPTION OF THE DRAWINGS

The invention, as well as its many advantages, may be further understood by the following detailed description and drawing in which:

FIG. 1 is a surface bore distribution diagram of a PVD (99.5% of Cr and 0.5% of Ag) in accordance with one embodiment of the present invention, provided that the number of the bores amplified by 300× per unit area is 2640 pcs/cm$^2$, the size of each bore is 8.3 μm, the number and size of the bores are measured in a square with each side equal to 0.25 mm.

DETAILED DESCRIPTION OF THE INVENTION

In the first preferred embodiment, a PC/ABS mirror casing coated with a double-layer antimicrobial coating is provided for the illustration of the present invention as follows:

(1) A plastic injection molded blank of the PC/ABS mirror casing is placed into a PVD vacuum equipment and processed by a vacuum process. When the vacuum level reaches 10$^{-2}$, the substrate is rinsed and activated (by a plasma glow activation) with the following processing conditions: the required current of the ion source is 0.5 A; the bias voltage is 150V; the duty ratio is 80%; the flow of argon is 100 SCCM; the flow of oxygen is 150 SCCM; the vacuum pressure in the furnace is 0.3 Pa; and the activation time is 10 minutes, so as to achieve the effect of cleaning and activating the surface of the substrate and enhancing the adhesion between an antimicrobial dechlorination film and the substrate.

(2) A metal film is coated on a surface of the plastic injection molded blank of the PC/ABS mirror casing with the following processing conditions of the mid-frequency sputtering method: the mid-frequency power is 9 KW; the bias voltage is 150V; the flow of argon is 100 SCCM; the vacuum pressure in the furnace is 0.3 Pa; the coating time is 20 minutes; and the metal film is made of pure Cu.

(3) The sample coated with the metal film by PVD is sprayed with an antimicrobial intermediate coating which is an UV coating added with an inorganic antimicrobial agent, and the UV coating is coated by the procedure as described below:

a. A UV paint layer added with 1% of nano silver antimicrobial agent is coated, wherein the paint layer has a thickness of 30 μm.

b. The plastic piece is sent into an infrared oven, and sprayed with paint. The paint coating is leveled and baked at 50° C. for 10 minutes.

c. The leveled and sprayed paint coating is placed into an ultraviolet curing furnace and processed by a radiation curing crosslink for 45 seconds.

(4) The sample sprayed with the antimicrobial intermediate coating is coated with an antimicrobial metal film by PVD, and the arc plating method is carried out with the processing conditions of: the required current of the target source is 100 A, the bias voltage is 150V, the flow of argon is 100 SCCM, the vacuum pressure in the furnace is 0.3 Pa, the coating time is 5 minutes; the target material of the antimicrobial metal film is an alloy target material containing 99.5% of Cr and 0.5% of Ag. The bore distribution of the surface of the alloy target material containing 99.5% of Cr and 0.5% of Ag and coated by PVD is shown in FIG. 1.

The sample is tested by the JIS Z2801:2000 antimicrobial-test for antimicrobial activity and efficacy standard, and the test results are listed in Table 1.

TABLE 1

| | | Bacterial count at different contact time or elutions | | | |
|---|---|---|---|---|---|
| Name of Testing Bacteria | Bacterial Liquid Solubility (cfu/mL) | / | Bacterial count within 0 h after vaccination | Bacterial count within 24 h after vaccination | Reduction Rate (%) |
| Escherichia coli ATCC8739 | 8.2 × 10$^5$ | Test Sample | / | <10 | 99.99 |
| | | Control Sample | 1.7 × 10$^5$ | 8.8 × 10$^8$ | |

TABLE 1-continued

| Name of Testing Bacteria | Bacterial Liquid Solubility (cfu/mL) | / | Bacterial count within 0 h after vaccination | Bacterial count within 24 h after vaccination | Reduction Rate (%) |
|---|---|---|---|---|---|
| *Staphylococcus Aureus* ATTCC6538P | $7.4 \times 10^5$ | Test sample | / | <10 | 99.96 |
| | | Control Sample | $1.4 \times 10^5$ | $5.1 \times 10^5$ | |

In the second preferred embodiment, a fiberglass reinforced PPO plastic substrate coated with a double-layer antimicrobial coating is provided for the illustration of the present invention as follows:

(1) The fiberglass reinforced PPO plastic substrate is placed into a PVD vacuum equipment and processed by a vacuum process. When the vacuum level reaches $10^{-2}$, the substrate is rinsed and activated (by a plasma glow activation) with the following processing conditions: the required current of the ion source 0.3 A, the bias voltage is 80V, duty ratio 50%, the flow of argon is 10 SCCM, the flow of oxygen is 50 SCCM, the vacuum pressure in the furnace is 0.1 Pa, the activation time is 5 minutes, so as to achieve the effect of cleaning and activating the surface of the substrate and enhancing the adhesion between an antimicrobial dechlorination film and the substrate.

(2) A metal film is coated on a surface of the fiberglass reinforced PPO plastic substrate with the following processing conditions of the mid-frequency sputtering method: the mid-frequency power is 6 KW; the bias voltage is 80V; the flow of argon is 20 SCCM; the vacuum pressure in the furnace is 0.1 Pa; the coating time is 10 minutes; and the metal film is made of Cu—Zn alloy.

(3) The sample coated with the metal film by PVD is sprayed with an antimicrobial intermediate coating which is an UV coating added with an inorganic antimicrobial agent, and the UV coating is coated by the procedure as described below:

a. An UV paint layer added with 10% of nano copper antimicrobial agent is coated, wherein the paint layer has a thickness of 10 μm.

b. The plastic piece is sent into an infrared oven, and sprayed with paint. The paint coating is leveled and baked at 70° C. for 3 minutes.

c. The leveled and sprayed paint coating is placed into a radiation curing furnace and processed by a radiation curing crosslink for 10 seconds.

(4) The sample sprayed with the antimicrobial intermediate coating is coated with an antimicrobial metal film by PVD, and the mid-frequency sputtering method is carried out with the processing conditions of: the mid-frequency power 9 KW, the bias voltage is 150V, the flow of argon is 100 SCCM, the vacuum pressure in the furnace is 0.3 Pa, the coating time is 10 minutes; the target material of the antimicrobial metal film is an alloy target material with a Cr content of 95% and an Ag content of 5%.

In the third preferred embodiment, a faucet made of PA6 added with fiberglass powder (enhanced PA6) and coated with a double-layer antimicrobial layer is provided for the illustration of the present invention as follows:

(1) The plastic substrate made of PA6 added with fiberglass powder (enhanced PA6) is placed into a PVD vacuum equipment and processed by a vacuum process. When the vacuum level reaches $10^{-2}$, the substrate is rinsed and activated (by a plasma glow activation) with the following processing conditions: the required current of the ion source 0.4 A; the bias voltage is 100V; the duty ratio 70%; the flow of argon is 50 SCCM; the flow of oxygen is 100 SCCM; the vacuum pressure in the furnace is 0.2 Pa; and the activation time is 8 minutes, so as to achieve the effect of cleaning and activating the surface of the substrate and enhancing the adhesion between an antimicrobial dechlorination film and the substrate.

(2) A metal film is coated on a surface of the plastic substrate made of PA6 added with fiberglass powder (enhanced PA6) with the following processing conditions of the mid-frequency sputtering method: the mid-frequency power is 8 KW; the bias voltage is 120V; the flow of argon is 70 SCCM; the vacuum pressure in the furnace is 0.2 Pa; the coating time is 15 minutes; and the metal film is made of pure Cr.

(3) The sample coated with the metal film by PVD is sprayed with an antimicrobial intermediate coating which is an UV coating added with an organic antimicrobial agent, and the UV coating is coated by the procedure as described below:

a. A UV paint layer added with 3% of Rohm and Haas Company's DCOIT antimicrobial agent is coated, wherein the paint layer has a thickness of 20 μm.

b. The plastic piece is sent into an infrared oven, and sprayed with paint. The paint coating is leveled and baked at 60° C. for 8 minutes.

c. The leveled and sprayed paint coating is placed into an ultraviolet curing furnace and processed by a radiation curing crosslink for 30 seconds.

(4) The sample sprayed with the antimicrobial intermediate coating is coated with an antimicrobial metal film by PVD, and the arc plating method is carried out with the processing conditions of: the required current of target source is 100 A, the bias voltage is 100V, the flow of argon is 70 SCCM, the vacuum pressure in the furnace is 0.2 Pa, the coating time is 3 minutes; the target material of the antimicrobial metal film is an alloy target material with a Cr content of 98% and an Ag content of 2%.

The sample is tested according to the JIS Z2801:2000 antimicrobial-test for antimicrobial activity and efficacy standard, and the test results are listed in Table 2.

TABLE 2

| Name of Testing Bacteria | Bacterial Liquid Solubility (cfu/mL) | Bacterial count at different contact time or elutions | | | Reduction Rate (%) |
|---|---|---|---|---|---|
| | | | Bacterial count within 0 h after vaccination | Bacterial count within 24 h of vaccination | |
| Escherichia Coli ATCC8739 | $8.5 \times 10^5$ | Test Sample | / | <10 | 99.99 |
| | | Control Sample | $1.8 \times 10^5$ | $9.6 \times 10^8$ | |
| Staphylococcus Aureus ATTCC6538P | $7.8 \times 10^5$ | Test Sample | / | <10 | 99.98 |
| | | Control Sample | $1.3 \times 10^5$ | $5.6 \times 10^5$ | |

In the fourth preferred embodiment, a refrigerator handle produced by a BMC thermosetting plastic blank coated with a double-layer antimicrobial layer is provided for the illustration of the present invention as follows:

(1) The BMC thermosetting plastic blank is placed into a PVD vacuum equipment and processed by a vacuum process. When the vacuum level reaches $10^{-2}$, the substrate is rinsed and activated (by a plasma glow activation) with the following processing conditions: the required current of the ion source 0.5 A; the bias voltage is 120V; the duty ratio is 60%; the flow of argon is 100 SCCM; the flow of oxygen is 100 SCCM; the vacuum pressure in the furnace is 0.2 Pa; and the activation time is 10 minutes, so as to achieve the effect of cleaning and activating the surface of the substrate and enhancing the adhesion between an antimicrobial dechlorination film and the substrate.

(2) A metal film is coated on a substrate surface of the BMC thermosetting plastic blank with the following processing conditions of the mid-frequency sputtering method: the mid-frequency power is 7 KW; the bias voltage is 100V; the flow of argon is 30 SCCM; the vacuum pressure in the furnace is 0.1 Pa; the coating time is 10 minutes; and the metal film is made of pure Cr.

(3) The sample coated with the metal film by PVD is sprayed with an antimicrobial intermediate coating which is an UV coating added with an organic antimicrobial agent, and the UV coating is coated by the procedure as described below:

a. A UV paint layer added with 6% of Troy Corporation's 10,10'oxybis-phenoxarsine (OBPA) antimicrobial agent is coated, wherein the paint layer has a thickness of 15 μm.

b. The plastic piece is sent into an infrared oven, and sprayed with paint. The paint coating is leveled and baked at 62° C. for 9 minutes.

c. The leveled and sprayed paint coating is placed into an ultraviolet curing furnace and processed by a radiation curing crosslink for 25 seconds.

(4) The sample sprayed with the antimicrobial intermediate coating is coated with an antimicrobial metal film by PVD, and the arc plating method is carried out with the processing conditions of: the required current of the target source is 80 A, the bias voltage is 80V, the flow of argon is 50 SCCM, the vacuum pressure in the furnace is 0.15 Pa, the coating time is 2 minutes; and the target material of the antimicrobial metal film is an alloy target material with a Cr content of 97% and an Ag content of 3%.

In the fifth preferred embodiment, an ABS mirror frame coated with a double-layer antimicrobial coating is provided for the illustration of the present invention as follows:

(1) A plastic substrate of the ABS mirror frame is placed into a PVD vacuum equipment and processed by a vacuum process. When the vacuum level reaches $10^{-2}$, the substrate is rinsed and activated (by a plasma glow activation) with the following processing conditions: the required current of the ion source 0.3 A; the bias voltage is 120V; the duty ratio is 60%; the flow of argon is 80 SCCM; the flow of oxygen is 120 SCCM; the vacuum pressure in the furnace is 0.2 Pa; and the activation time is 5 minutes, so as to achieve the effect of cleaning and activating the surface of the substrate and enhancing the adhesion between an antimicrobial dechlorination film and the substrate.

(2) A metal film is coated on a substrate surface of the ABS mirror frame with the following processing conditions of the mid-frequency sputtering method: the mid-frequency power is 7 KW; the bias voltage is 100V; the flow of argon is 70 SCCM; the vacuum pressure in the furnace is 0.2 Pa; the coating time is 20 minutes; and the metal film is made of pure Cu.

(3) The sample coated with the metal film by PVD is sprayed with an antimicrobial intermediate coating which is an UV coating added with an organic antimicrobial agent, and the UV coating is coated by the procedure as described below:

a. A UV paint layer added with 10% of PolyChem Alloy Inc's "PolySept L" antimicrobial agent is coated, wherein the paint layer has a thickness of 10 μm.

b. The plastic piece is sent into an infrared oven, and sprayed with paint. The paint coating is leveled and baked at 55° C. for 10 minutes.

c. The leveled and sprayed paint coating is placed into an ultraviolet curing furnace and processed by a radiation curing crosslink for 10 seconds.

(4) The sample sprayed with the antimicrobial intermediate coating is coated with an antimicrobial metal film by PVD, and the mid-frequency sputtering method is carried out with the processing conditions of: mid-frequency power 8 kW, the bias voltage is 100V, the flow of argon is 20 SCCM, the vacuum pressure in the furnace is 0.1 Pa, the coating time is 10 minutes; and the target material of the antimicrobial metal film is an alloy target material with a Cr content of 96% and an Ag content of 4%.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A method of preparing a double-layer antimicrobial coating, comprising the steps of:
   (1) placing a plastic substrate in a physical vapor deposition (PVD) vacuum equipment to carry out a vacuum process, and then rinsing and activating the substrate when a vacuum level reaches $10^{-2}$ Pa to obtain an activated substrate;

(2) coating a metal film on a surface of the activated substrate by vacuum coating;

(3) spraying the substrate coated with the metal film with an antimicrobial intermediate coating, wherein the antimicrobial intermediate coating is added with an organic antimicrobial agent selected from the group consisting of 3-(trimethoxysilyl)propyldimethyloctadecylammonium, 10,10'oxybis-phenoxarsine, and phosphate complex; and (4) coating the substrate having the sprayed antimicrobial intermediate coating with an antimicrobial metal film by PVD to obtain a double-layer antimicrobial layer; wherein the antimicrobial metal film formed by PVD has a low density and includes a large number of bores, such that the antimicrobial agent of the antimicrobial intermediate coating can pass through the bores and move to a surface of the antimicrobial metal film, so as to kill the bacteria or suppress their growth.

2. The method of preparing a double-layer antimicrobial coating as recited in claim 1, wherein the plastic substrate as described in the step (1) is one selected from the group of thermoplastic and thermosetting plastic, and the thermoplastic is one selected from the group of ABS, PC/ABS, HIPS, PC, PPO, PP, PERT, HDPE, PA6, PA66, ABS/TPU, fiberglass reinforced PA6 and fiberglass reinforced PP, and the thermosetting plastic is BMC.

3. The method of preparing a double-layer antimicrobial coating as recited in claim 1, wherein the activation as described in the step (1) is a plasma glow activation performed under the conditions of: a current of an ion source falling within a range of 0.3-0.5 A, a bias voltage falling within a range of 80-150V, a duty ratio falling within a range of 50%-80%, the flow of argon falling within a range of 10-100 SCCM, the flow of oxygen falling within a range of 10-150 SCCM, a vacuum pressure in the furnace falling within a range of 0.1-0.3 Pa, and an activation time falling within a range of 5-10 minutes.

4. The method of preparing a double-layer antimicrobial coating as recited in claim 1, wherein the method of coating the metal film onto the substrate surface by the vacuum process as described in the step (2) adopts a mid-frequency sputtering method, and the mid-frequency sputtering method is carried out with the processing conditions including a mid-frequency power falling within a range of 6-9 kW, a bias voltage falling within a range of 80-150V, a flow of argon falling within a range of 20-100 SCCM, a vacuum pressure inside a furnace falling within a range of 0.1-0.3 Pa, a coating time falling within a range of 10-20 minutes, and the metal film being made of at least one material selected from the group of Cu, Cr, and Cu—Zn alloy.

5. The method of preparing a double-layer antimicrobial coating as recited in claim 1, wherein the antimicrobial intermediate coating is one selected from the group of an UV-curing paint, a baking paint, an electrophoretic paint and an electrostatic powder paint.

6. The method of preparing a double-layer antimicrobial coating as recited in claim 1, wherein the method of spraying the antimicrobial intermediate coating onto the substrate coated with the metal film as described in the step (3) comprises the steps of: spraying a paint layer added with 1%-10% of an antimicrobial agent onto a plastic substrate; sending the plastic substrate into an infrared oven; leveling and baking the paint coating; and performing a radiation curing crosslink to the paint coating in an ultraviolet curing furnace, wherein the radiation curing crosslink time falls within a range of 10-45 seconds; the paint layer has a thickness falling within a range of 10-30 μm; the baking temperature falls within a range of 50-70° C., the baking time falls within a range of 3-10 minutes; the paint layer is one selected from the group of an UV paint layer, an electrophoretic paint layer, and a powder paint layer.

7. The method of preparing a double-layer antimicrobial coating as recited in claim 1, wherein the antimicrobial metal film coated by the PVD as described in the step (4) adopts an arc plating method or a mid-frequency sputtering method.

8. The method of a preparing double-layer antimicrobial coating as recited in claim 7, wherein the arc plating method is carried out with the processing conditions including a current of target source falling within a range of 60-100 A, a bias voltage falling within a range of 80-150V, a flow of argon falling within a range of 20-100 SCCM, a vacuum pressure inside the furnace falling within a range of 0.1-0.3 Pa, a coating time falling within a range of 1-5 minutes, and the mid-frequency sputtering method is carried out with the processing conditions including a mid-frequency power falling within a range of 6-9 kW, a bias voltage falling within a range of 80-150V, a flow of argon falling within a range of 20-100 SCCM, a vacuum pressure inside the furnace falling within a range of 0.1-0.3 Pa, a coating time falling within a range of 5-10 minutes, and a target material of the antimicrobial metal film being an alloy target material with a Cr content of 95%-99.5% and an Ag content of 5%-0.5%.

* * * * *